(12) United States Patent
Bell et al.

(10) Patent No.: US 7,479,395 B2
(45) Date of Patent: Jan. 20, 2009

(54) METHOD OF MONITORING A PRODUCTION PROCESS USING A LINEAR COMBINATION OF MEASURED VARIABLES WITH SELECTED WEIGHTS

(75) Inventors: Ferdinand Bell, München (DE); Dirk Knobloch, München (DE); Knut Voigtländer, Dresden (DE); Jan Zimpel, Dresden (DE)

(73) Assignee: Infineon Technologies AG, Munich (DE)

( * ) Notice: Subject to any disclaimer, the term of this patent is extended or adjusted under 35 U.S.C. 154(b) by 1255 days.

(21) Appl. No.: 10/205,080

(22) Filed: Jul. 25, 2002

(65) Prior Publication Data

US 2003/0008507 A1    Jan. 9, 2003

Related U.S. Application Data

(63) Continuation of application No. PCT/DE00/00249, filed on Jan. 25, 2000.

(51) Int. Cl.
  *H01L 21/00* (2006.01)
(52) U.S. Cl. .......................................... 438/9; 438/706
(58) Field of Classification Search ............. 438/9, 438/7, 706, 710, 712; 216/60
  See application file for complete search history.

(56) References Cited

U.S. PATENT DOCUMENTS

| | | | | |
|---|---|---|---|---|
| 4,609,426 A | * | 9/1986 | Ogawa et al. | 216/60 |
| 5,658,423 A | * | 8/1997 | Angell et al. | 438/9 |
| 5,728,253 A | | 3/1998 | Saito et al. | |
| 5,737,496 A | | 4/1998 | Frye et al. | |
| 5,739,051 A | | 4/1998 | Saito | |
| 5,864,773 A | | 1/1999 | Barna et al. | |
| 5,877,032 A | | 3/1999 | Guinn et al. | |
| 6,153,115 A | * | 11/2000 | Le et al. | 216/60 |
| 6,381,008 B1 | * | 4/2002 | Branagh et al. | 356/72 |
| 6,420,194 B1 | * | 7/2002 | Reitman | 438/9 |
| 6,535,785 B2 | * | 3/2003 | Johnson et al. | 700/121 |
| 6,586,262 B1 | * | 7/2003 | Saito et al. | 438/9 |

FOREIGN PATENT DOCUMENTS

| EP | 0 602 855 A1 | 6/1994 |
|---|---|---|
| WO | WO 99/21210 | 4/1999 |

OTHER PUBLICATIONS

Whilte et al. "Spatial characterization of wafer state using principal component analysis of optical emission spectra in plasma etch" IEEE transations on semiconductor manufacturing, vol. 10, No. 1, Feb. 1997.*

* cited by examiner

*Primary Examiner*—Kin-Chan Chen
(74) *Attorney, Agent, or Firm*—Laurence A. Greenberg; Werner H. Stemer; Ralph E. Locher (57) ABSTRACT

The invention relates to a method for monitoring a manufacturing process, which by using a linear combination of measured variables with judiciously chosen weighting, produces a suitable (optimal) signal for determining each parameter. The extraction of the parameters from the measured variables is thus greatly simplified and in many cases becomes actually possible for the first time. According to the invention, large amounts of data may now be prepared, such that the crucial information (parameters) can be obtained from the data, almost in real time, or in real time.

20 Claims, 9 Drawing Sheets

METHOD OF MONITORING A PRODUCTION PROCESS USING A LINEAR COMBINATION OF MEASURED VARIABLES WITH SELECTED WEIGHTS

CROSS-REFERENCE TO RELATED APPLICATION

This application is a continuation of copending International Application No. PCT/DE00/00249, filed Jan. 25, 2000, which designated the United States and was not published in English.

BACKGROUND OF THE INVENTION

Field of the Invention

The present invention relates to a method of monitoring a production process. The present invention relates in particular to a method of monitoring a production process for processing a semiconductor substrate in semiconductor fabrication.

Modern industrial production is generally characterized by a high level of automation. In the semiconductor industry, in particular, a high level of automation is imperative in order to be able to be competitive internationally.

During the production and processing of semiconductor substrates to form integrated semiconductor circuits, a large number of production processes and processing processes are used. Examples that may be mentioned here are deposition processes for producing material layers and etching processes for structuring these layers. These production processes have to be monitored thoroughly since, because of their complexity, unnoticed faults or poorly coordinated process conditions can lead to the production of faulty semiconductor circuits. In order to be able to perform this monitoring efficiently, there is generally a desire to characterize the production process by analyzing specific measured variables that are determined during the production process, in order, if appropriate, to be able to intervene in a controlling manner.

In particular, in the case of etching for structuring material layers, the etching time is a critical parameter in order to achieve a high-quality result. If the etching time is too short, the layer that will be etched is only incompletely removed. In the event of excessively long etching, for example, active regions may begin to be etched or structures may be underetched. Both conditions must be avoided by using suitable methods for detecting the correct end point.

One possible method for detecting the correct end point is, for example, disclosed by U.S. Pat. No. 5,877,032. In that document, a method of determining the end point of a plasma etching process is described, in which the optical emission of the plasma is used to determine the end point. The background to this method is the fact that, during the etching process, a layer located on a substrate is etched through, and in the process, the substrate lying underneath or the layer lying underneath is exposed. The interaction of the etching gas with the exposed substrate or the exposed layer may be detected spectroscopically as a change in the emission spectrum of the plasma. According to U.S. Pat. No. 5,877,032, this change is compared with a large number of predefined reference curves and conclusions about the end point of the plasma etching process are drawn from the comparison.

U.S. Pat. No. 5,739,051 likewise discloses a method of determining the end point of a plasma etching process. In this method, the optical emission of the plasma is likewise used to determine the end point. Emission lines that are characteristic of the interaction of the etching gas with the exposed substrate are used for the assessment.

It is normally the case in industrial plants that optical filters are used, depending on the chemical reactions proceeding in the plasma, in order to be able to track the time profile of the intensities in fixedly predefined wavelength ranges. This procedure is not practicable in particular in chambers in which products with different chemical compositions are run alternately. The detection of the end point in various optical ranges in this case requires a high level of mechanical effort and expenditure of time to change the filters. Furthermore, the selection of the wavelength ranges lies within the responsibility of the process engineer. The selection of unfavorable wavelength ranges for end point detection is not ruled out in this case.

Therefore, according to U.S. Pat. No. 5,658,423, a method based on "principal component analysis" is proposed, in which the development over time of the entire emission spectrum from about 240 to 600 nm is used to determine the end point. By using the principal component analysis, the quantity of accumulated data is reduced to a few basic patterns, as they are known, and their development over time is used for detecting the end point. In this way, the detection of the end point is no longer based on the assessment of a single emission wavelength, but on the change in the entire spectrum available. In principle, however, even in the method according to U.S. Pat. No. 5,658,423, reference values must be provided, in order to be able to draw conclusions about the correct end point from the comparison between the currently measured variables and the reference values. Furthermore, in the method according to U.S. Pat. No. 5,658,423, the end point signal is determined from the difference between two spectral matrices. The relevance of this change with respect to determining the end point has to be ensured again each time.

To determine the correct end point without corresponding reference values, U.S. Pat. No. 5,737,496 proposes using a neural network. The neural network is trained by using a large number of determined measured variables, so that it can subsequently be used for detecting the end point. However, it has been shown that neural networks often learn false signals and patterns, so that misinterpretation can occur. Faulty training of the neural network arises, for example, as a result of a change in the emission spectra on account of aging phenomena in the sensors or the occurrence of chamber contamination. Therefore, in U.S. Pat. No. 5,864,773, a virtual sensor system, as it is called, is proposed, in which these changes are taken into account before the actual assessment of the measured variables. The intention is to provide a virtual sensor that is free of the effects of chamber-specific or process-specific faults. However, since even in this case it is necessary to fall back on the experience of the operating personnel, faults and changes that occur unexpectedly cannot be taken into account automatically.

SUMMARY OF THE INVENTION

It is accordingly an object of the invention to provide a method of monitoring a production process, which reduces or entirely avoids the aforementioned disadvantages.

In particular, it is an object of the invention to provide a method of monitoring a production process, which is capable of extracting the critical information, that is to say important characteristic variables, from large quantities of data.

With the foregoing and other objects in view there is provided, in accordance with the invention, a method of monitoring a production process that has the following steps:

a) a large number of measured variables is determined at predefined times;

b) at least one linear combination is formed from the large number of measured variables, the weights of the linear combination are selected such that a predefined curve shape is approximated; and c) at least one characteristic variable is determined from the linear combination.

The method has the advantage that, by using a linear combination of the measured variables with suitably selected weights, a (optimal) signal suitable for determining the respective characteristic variable is generated, which considerably simplifies the extraction of the characteristic variable from the measured variables which, in many cases, becomes possible at all for the first time. Here, in the following text, the term linear combination should be understood not only as the procedure of linearly combining measured variables, but also the signal obtained in this way.

During the monitoring of production or processing processes, very large quantities of data may accumulate. This data contains very accurate information about the monitored production or processing process. However, it is generally difficult to extract the critical information from the data. By using the inventive method, it is now possible to prepare the data in such a way that the critical information (characteristic variables) can be obtained from the data virtually in real time or in real time. Accordingly, with the method, data which has hitherto been used only for the subsequent (offline) analysis of the process can now be used for online monitoring of production or processing processes.

Furthermore, the method provides the advantage that in the event of a change in the production process, the necessary adaptation to the extraction of the characteristic variable can be performed merely by adapting the corresponding measuring software, and no manual working steps, such as the replacement of optical filters, are necessary.

According to a preferred embodiment, the measured variables used are the intensities of various wavelengths in an emission spectrum. As a rule, emission spectra contain very detailed information about the process on which the radiation emission is based, for example a chemical reaction. However, very large quantities of data accumulate during the recording of such spectra, from which, using conventional methods, the critical information can be extracted only with great difficulty. By using the inventive method, it is now possible to prepare the data from an emission spectrum in such a way that the critical information (characteristic variables) can be obtained from the data virtually in real time or in real time. Accordingly, emission spectra can be used with the inventive method for the online monitoring of production or processing processes. In this case, it is particularly preferable for the intensities of various wavelengths in a spectral range between 200 and 950 nm to be used.

According to a preferred embodiment, the emission spectrum from a plasma process, in particular a plasma etching process, is used. Plasma etching processes for structuring material layers play an important part in semiconductor fabrication. The dimensions of the structures produced critically depend on the quality of the etching process used. The emission spectrum of the plasma contains a large amount of information which is needed in order to monitor the plasma process. Highly developed sensor systems such as "optical emission spectroscopy (OES)" or "residual gas analysis (RGA)" can be used to record the spectra. In this case, it is particularly preferable if the end point of the plasma process is determined as the characteristic variable.

According to a further preferred embodiment, the predefined curve shape used is a step-like function. Step-like functions, such as a hyperbolic tangent function, can be examined relatively easily with appropriate evaluation algorithms to see whether the step has already been passed through or not, that is to say whether the value of the function has already jumped from a low value to a higher value. Therefore, if the characteristic variable that will be determined is linked to the occurrence of the step, the characteristic variable can be relatively simply determined automatically. In this case, it is preferable in particular if the step-like function has at least one free parameter to match to the characteristic variable to be determined.

According to a further preferred embodiment, to determine the weights of the linear combination, the measured variables at the predefined times are arranged in a matrix, and a principal component analysis is carried out on the basis of this matrix. The principal component analysis is a method to express a matrix A by using its principal vectors or principal components. In order to calculate the principal components, a series of methods can be used. For example, singular value decomposition (SVD) of the matrix A can be calculated. As an alternative, the eigenvalues and eigenvectors of the correlation matrix ($A^TA$) of the matrix A can also be calculated. Furthermore, other methods for the decomposition of a matrix, such as "(nonlinear) partial least squares" of a matrix A can also be used.

The principal component analysis is preferably implemented using a singular value decomposition, so that the matrix $A^{m \times n}$ is decomposed into two orthogonal matrices $U^{m \times n}$ and $V^{m \times n}$ and a diagonally filled matrix $\Sigma$ with the singular values $\sigma_i$, it being true that:

$$A = U\Sigma V^T = \Sigma_i \sigma_i u_i v_i^T.$$

Here, the "left-hand" eigenvectors $u_i$ form the matrix $U^{m \times m}$, while the "right-hand" eigenvectors $v_i$ form the matrix $V^{n \times n}$. The singular values $\sigma_i$ are normally arranged in order of magnitude and represent the proportion which the associated dyadic product $u_i v_i^T$ has in the formation of the overall matrix A. The dyadic products $u_i v_i^T$, which have only small singular values $\sigma_i$, generally do not carry information about the monitored process. Accordingly, real measured matrices of measured variables are generally represented sufficiently well by the dyadic products $u_i v_i^T$ with the 3 to 15 largest singular values $\sigma_i$.

According to a further preferred embodiment, to determine the weights of the linear combination, a function based on the predefined curve shape and the linear combination is minimized or maximized. In this case, it is preferable if the important principal components of the measured variable matrix are determined by the minimization (or maximization) of the function. By using the minimization (or maximization) of the function, it is possible in a straightforward manner to define those principal components which must be taken into account in order to be able to approximate the predefined curve shape with sufficient accuracy. Furthermore, it is preferable if, as a result of the minimization of the function, the free parameter of the step-like function is determined. In this way, an optimum signal profile for the measured variable to be determined can be defined in a self-consistent way.

According to a further preferred embodiment, to determine the characteristic variable, smoothing of the linear combination is carried out. As a rule, the measured variables have a noise component which is also found again in a linear combination of the measured variables. In order that no erroneous evaluation is performed because of the noise, it is preferable to suppress the noise component by smoothing the linear combination to such an extent that the characteristic variable can be determined correctly. Here, it is particularly preferable if the smoothing of the linear combination is achieved by using a zero-phase filter. By suppressing the noise component, qualitative criteria, such as the occurrence of a local maximum or the occurrence of a point of inflection, can be used to determine the characteristic variable. As compared with quantitative criteria, such as exceeding specific threshold values, qualitative criteria have the advantage that they depend to a far less extent on the respective absolute magnitude of the measured values and can therefore be used more robustly over a greater value range.

In order to increase the robustness of the method, it may be expedient to include the results of a number of sample runs or production runs in the definition of the weights (coefficients) for the linear combination. For this reason, according to a further preferred embodiment, the measured variables from a number of sample and/or production runs are used to determine the weights of the linear combination. In this case, it is preferable if the measured variables from a number of sample and/or production runs are arranged in a matrix (block matrix) and a principal component analysis is carried out on the basis of this matrix.

Other features which are considered as characteristic for the invention are set forth in the appended claims.

Although the invention is illustrated and described herein as embodied in a method of monitoring a production process, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DESCRIPTION OF THE PREFERRED EMBODIMENTS

Figure 1:
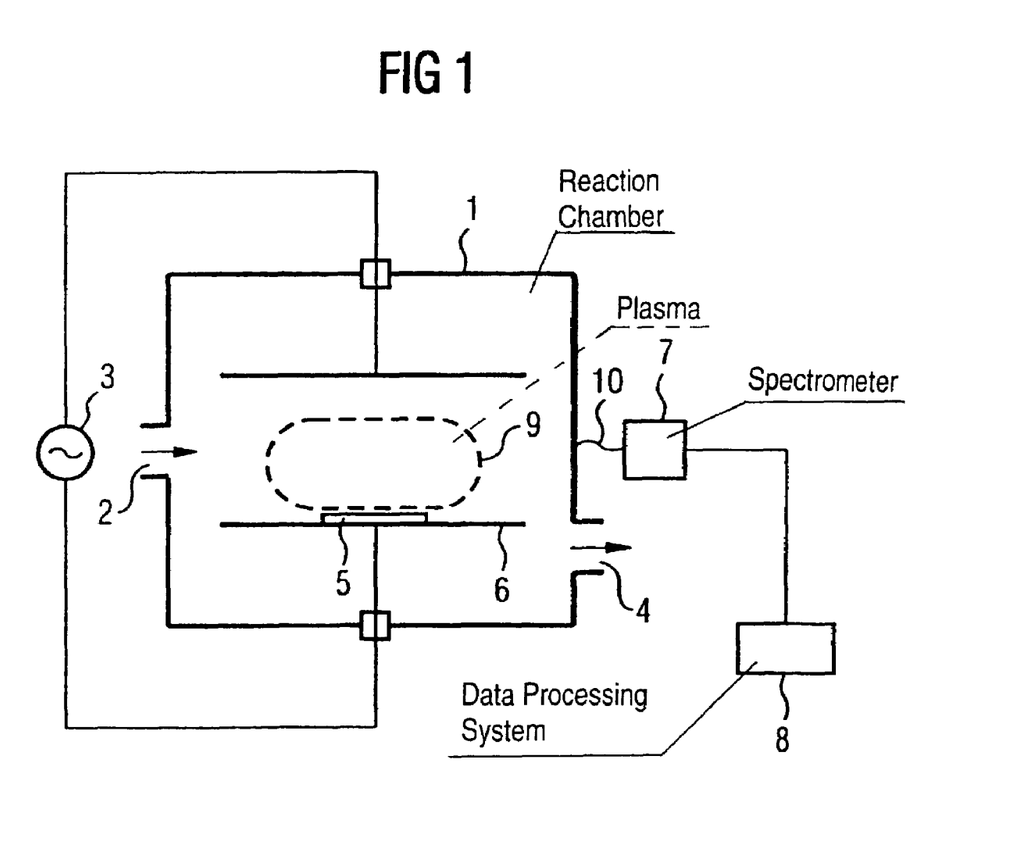
FIG. 1 shows a schematic representation of an apparatus for carrying out a first embodiment of the inventive method.

Referring now to the figures of the drawing in detail and first, particularly, to FIG. 1 thereof, there is shown a schematic representation of an apparatus for carrying out a first embodiment of the inventive method. The significant components of this apparatus are a reaction chamber 1 in which, for example, a plasma etching process (e.g. RIE) can be carried out. The etching gas is led via an inlet 2 into the reaction chamber 1, where it is ionized and converted into a plasma. The plasma 9 is generated and maintained by an RF voltage which is applied capacitively and is provided by an RF source 3. The reaction products of the etching are removed from the reaction chamber 1 through an outlet 4. The etching gas used is an etching gas mixture of $CF_4$, $CHF_3$ and argon. The homogeneity of the plasma is improved by a magnetic field (not shown) of about 60 gauss. The power used to generate and maintain the plasma is about 1200 watts. The pressure in the reaction chamber 1 is about 150 mtorr in this case.

In the present example, the plasma is used to etch contact holes in a silicon dioxide layer which is arranged on a silicon wafer 5. For this purpose, the silicon wafer 5 is placed on a holder 6 in the reaction chamber 1. In modern semiconductor products, such as memories or processors, the contact holes, which are generally used to connect the diffusion regions (active regions) of the transistors, have a very small opening ratio. The requirements on detecting the correct end point of the etching, at which the contact holes reach the silicon substrate, are correspondingly high. If the etching time is too short, the contact holes are not completely opened and the transistors are not connected. If the etching time is too long, the active-regions of the transistors begin to be etched strongly. Both can lead to total failure of the integrated circuit.

In order to determine the correct end point of the etching, an optical waveguide 10 is arranged at a window of the reaction chamber 1, and leads to a multichannel spectrometer 7. In the present exemplary embodiment, a multichannel spectrometer from Hamamatsu with the type designation C7460 was used for detecting the optical emission of the plasma. This multichannel spectrometer 7 has 1024 channels, which are distributed uniformly over a wavelength range from 200 to 950 nm. With the multichannel spectrometer used, a maximum scanning rate of 50 per second can be achieved. In the present exemplary embodiment, the average emission spectrum of the plasma is measured every 2 seconds. The multichannel spectrometer 7 is connected to a data processing system 8, which continuously records, evaluates and stores the registered spectra.

If, then, contact hole etching is carried out, the intensities of various wavelengths (1024 different wavelengths in the present case) are recorded over a time period of about 3 min. The resulting measured values are arranged in the form of a matrix $\Lambda(\lambda, t)$. In this case, the time profile of a specific wavelength corresponds exactly to one line of the matrix $\Lambda(\lambda, t)$. Accordingly, the emission spectrum at a specific time is given by exactly one column of the matrix $\Lambda(\lambda, t)$. However, this arrangement is not imperative, for example, the time profiles of the wavelength can also be arranged as the columns of the matrix $\Lambda(\lambda, t)$. In the present exemplary embodiment, the matrix $\Lambda(\lambda, t)$ has 1024 rows and 100 columns.

In order to determine the correct weights for the linear combination from the intensities of the measured wavelengths, a principal component analysis is then carried out on the basis of the matrix $\Lambda(\lambda, t)$. To this end, first a matrix $\Lambda_0(\lambda, t)$ is drawn up during trial etching and the weights are determined, which are then used for subsequent etchings. The principal component analysis is implemented by using a singular value decomposition, so that the matrix $\Lambda_0(\lambda, t)$ is decomposed into two orthogonal matrices $U_0$ and $V_0$ and a diagonally filled matrix $\Sigma_0$ with the singular values $\sigma^0_i$, it being true that:

$$\Lambda_0(\lambda,t)=U_0\Sigma_0 V_0^T=\Sigma_i \sigma^0_i u^0_i (v^0_i)^T.$$

Figure 2A:
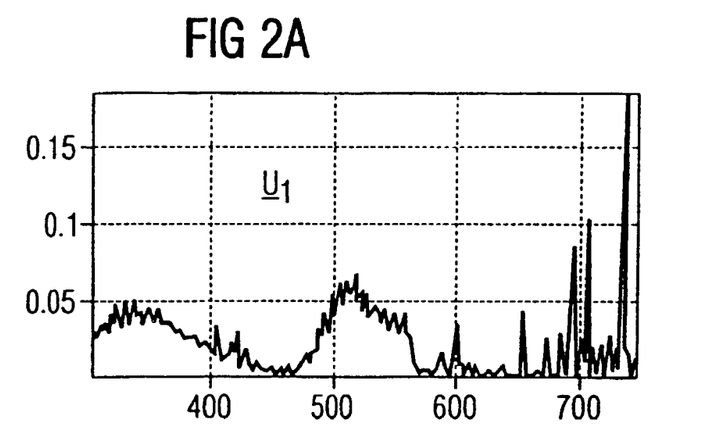
FIGS. 2A-2C show representations of the first three left-hand eigenvectors of a spectral matrix.
Figure 2B:
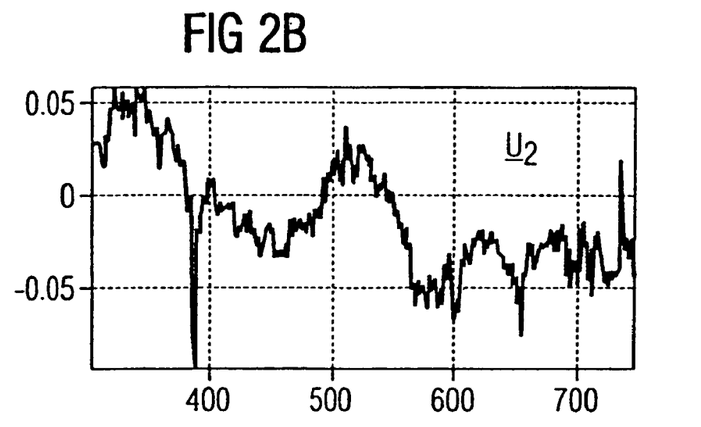
Figure 2C:
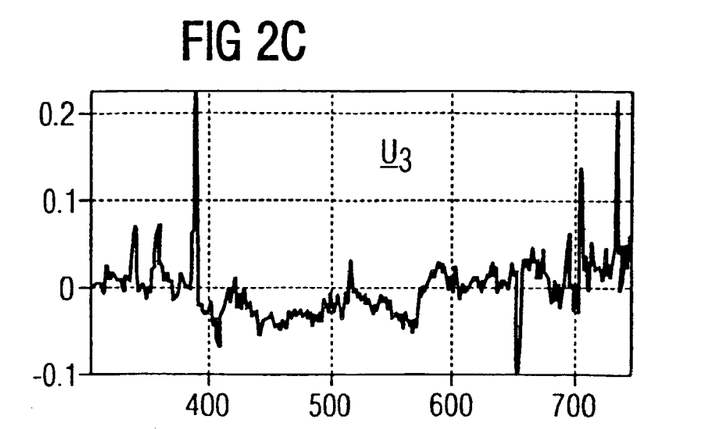
Figure 3A:
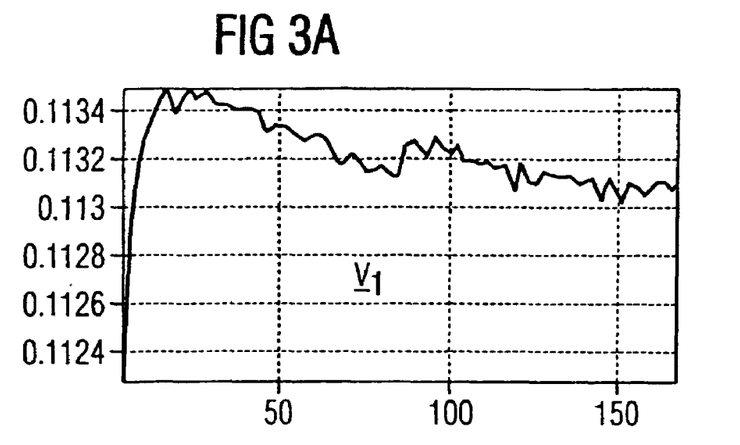
FIGS. 3A-3C show representations of the corresponding first three right-hand eigenvectors of a spectral matrix.
Figure 3B:
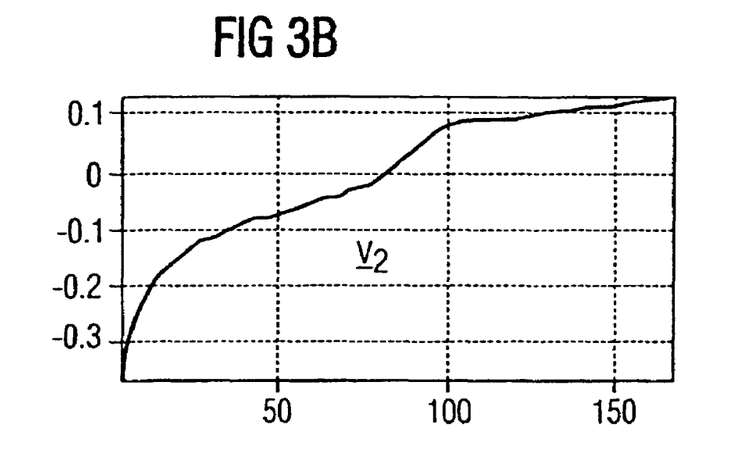
Figure 3C:
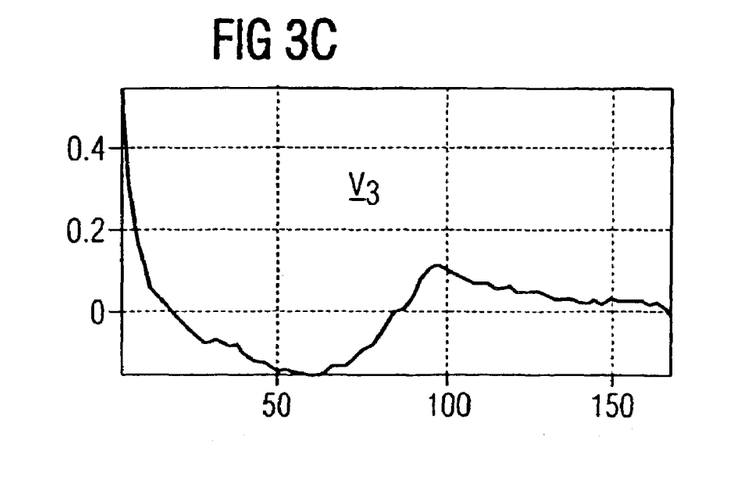

Here, the "left-hand" eigenvectors $u^0_i$ form the matrix $U_0$, while the "right-hand" eigenvectors form the matrix $v^0_i$. FIGS. 2A-2C show representations of the first three left-hand eigenvectors $u^0_i$ from the matrix $\Lambda_0(\lambda, t)$. That is to say the left-hand eigenvectors $u^0_i$ with the three largest singular values $\sigma^0_i$. FIGS. 3A-3C show representations of the corresponding first three right-hand eigenvectors $v^0_i$ of the matrix $\Lambda_0(\lambda, t)$. The columns $u^0_i$ of the matrix $U_0$ can be interpreted as a basic wavelength pattern, while the columns $v^0_i$ of the matrix $V_0$ can be interpreted as basic timing signals.

In order to determine a suitable linear combination of the measured variables, the following approach is now used:

$$Y_0(t)=\Sigma_i \Lambda_0(\lambda,t)^T u^0_i c_i.$$

Here, the index i indicates the most important left-hand principal components $u^0_i$ from the matrix $\Lambda_0(\lambda, T)$. How many and which of the most important principal components $u^0_i$ can actually be taken into account is determined by the following minimization of a quality function. In addition, the still unknown coefficients $c_i$ are defined in the following minimization of the quality function. Once the most important principal components $u^0_i$ are defined and the coefficients ci are determined, the linear combination of the measured variables is also defined as a result. On account of the orthogonality of the left-hand principal components $u^0_i$, the function $Y_0(t)$ can also be written in the following form:

$$Y_0(t)=\Sigma_i v^0_i(t)\sigma^0_i c_i.$$

The function $Y_0(t)$ is a function of the time t, which can be matched to a predefined curve shape by using the coefficients $c_i$. In this case, the predefined curve shape is chosen such that the important characteristic variable, in this case the end point of the etching, can be extracted relatively easily from the linear combination. A typical example of such a curve shape is a hyperbolic tangent function:

$$Y_{MO}(t)=0.5(\tan h[(t-t_{EP})/\delta]+1).$$

Here, the parameter $\delta$ is a measure of the desired slope with which the function $Y_{MO}(t)$ jumps from its initial value ($\approx 0$) to its final value ($\approx 1$). In this example, this parameter is predefined externally and is not a variable in the optimization which now follows. The parameter $t_{EP}$ specifies the time at which the function $Y_{MO}(t)$ jumps from its initial value ($\approx 0$) to its final value ($\approx 1$). This parameter $t_{EP}$ is not predefined externally but is defined in the optimization which now follows, so that the end point obtained from the trial run and the parameter $t_{EP}$ agree as well as possible. In this exemplary embodiment, this is achieved by minimizing the quality function Q. Here:

$$Q^2=\Sigma_t(Y_0(t,c_i)-Y_{MO}(t,t_{EP}))^2/N$$

with the normalization factor, $$N=\Sigma_t(Y_{MO}(t,t_{EP})-\Sigma_{t'}Y_{MO}(t',t_{EP}))^2.$$

The sum $\Sigma_t$ (or $\Sigma_{t'}$) here represents a sum of the respective function values at the predefined times. By using the minimization of the quality function Q, the most important principal components $v^0_i$ are selected, the parameter $t_{EP}$ is optimized, and the coefficients ci are determined. The latter is possible without difficulty because of the orthonormality of the right-hand eigenvectors voi. Thus, the relationship:

$$C^{opt}_i(t_{EP})=1/\sigma^0_i \Sigma_t v^0_i(t) Y_{MO}(t,t_{EP})$$

results for the optimum coefficients $C^{opt}_i$, which of course still depend implicitly on the parameter $t_{EP}$. The choice of the most important principal component $u^0_i$ and $v^0_i$ is likewise easy to solve, since again, on account of the orthogonality property, the contribution of each principal component to the reduction in the quality function Q can be specified directly. For a specific preselection of principal components, it is merely necessary to select those principal components that have the largest coefficients $c^{opt}_i$ in terms of magnitude.

Figure 4:
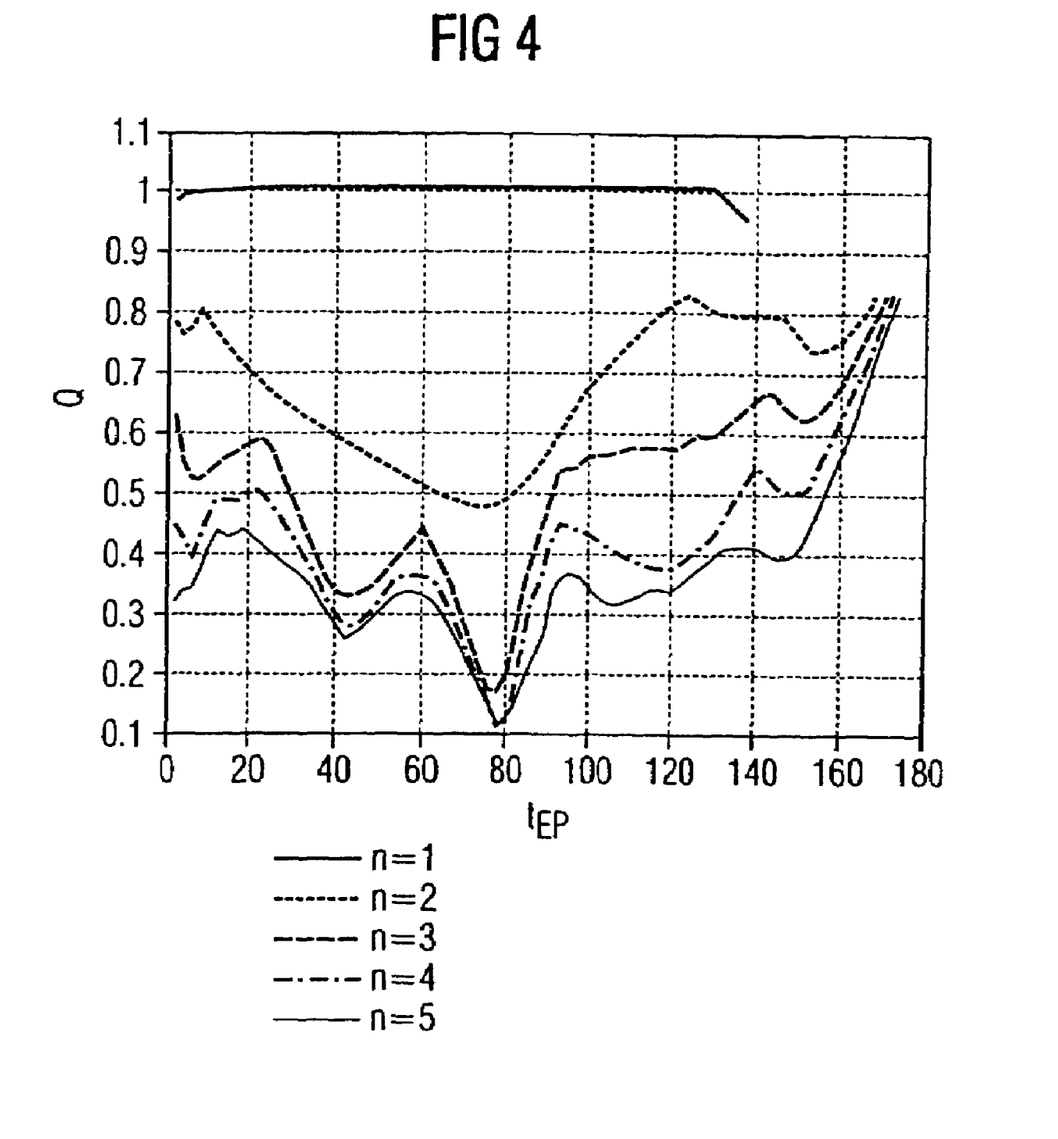
FIG. 4 is a graph of the achievable model quality as a function of the end point $t_{Ep}$ and the number of principal components taken into account.

As an example, FIG. 4 shows a graph of the model quality which can be achieved as a function of the end point $t_{EP}$ and the number of principal components taken into account. The optimum selection for the parameter $t_{EP}$ (that point at which the steepest end point signal can be generated) is found by using a one-dimensional numerical optimization. In this case, it is expedient to use a higher-order grid search and then a local gradient-oriented optimization in order to find the optimum $t_{EP}^{opt}(n)$ as a function of the number of principal components taken into account. In this way, disturbances from local minima can be avoided.

Figure 5:
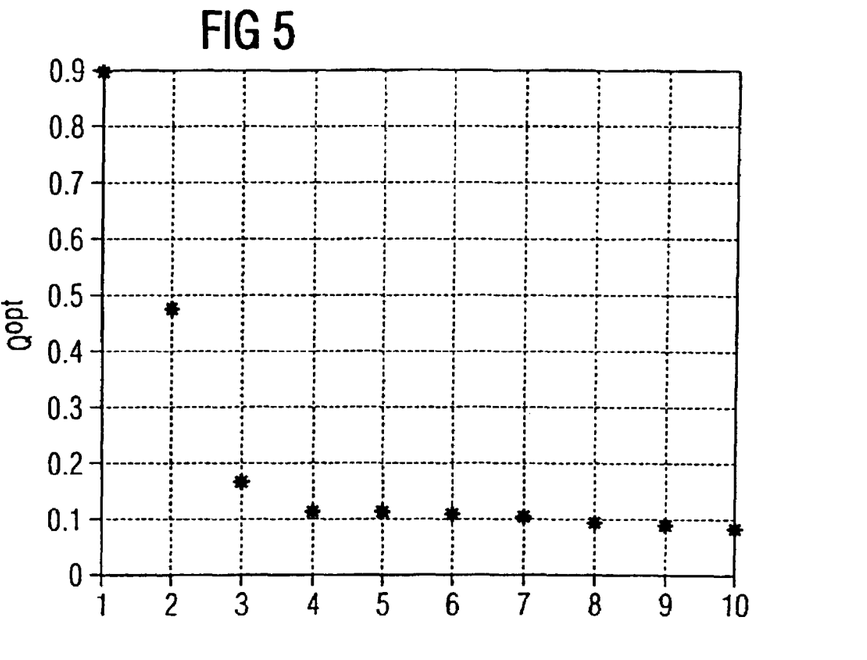
FIG. 5 is a graph of the achievable model quality with an optimum $C^{opt}_i$ and $t_{Ep}$ as a function of the number of principal components taken into account.

FIG. 5 shows a graph of the achievable model quality $Q^{opt}$ with optimum coefficients $c^{opt}_i$ and $t_{EP}^{opt}$ as a function of the number of principal components taken into account. On the basis of this graph, the single parameter that still needs to be defined, the number of principal components to be taken into account, can finally be defined. In FIG. 5, it can be seen that a sufficient model quality is already achieved with four selected principal components.

The trial etching has therefore been evaluated, and the weights of the linear combination of the measured variables have been defined. From the selected right-hand principal components and the optimum coefficients $c^{opt}_i$, an "end point pattern" $u_{EP}$ can now be formed:

$$u_{EP}=\Sigma_i u_i c^{opt}_i.$$

Figure 6:
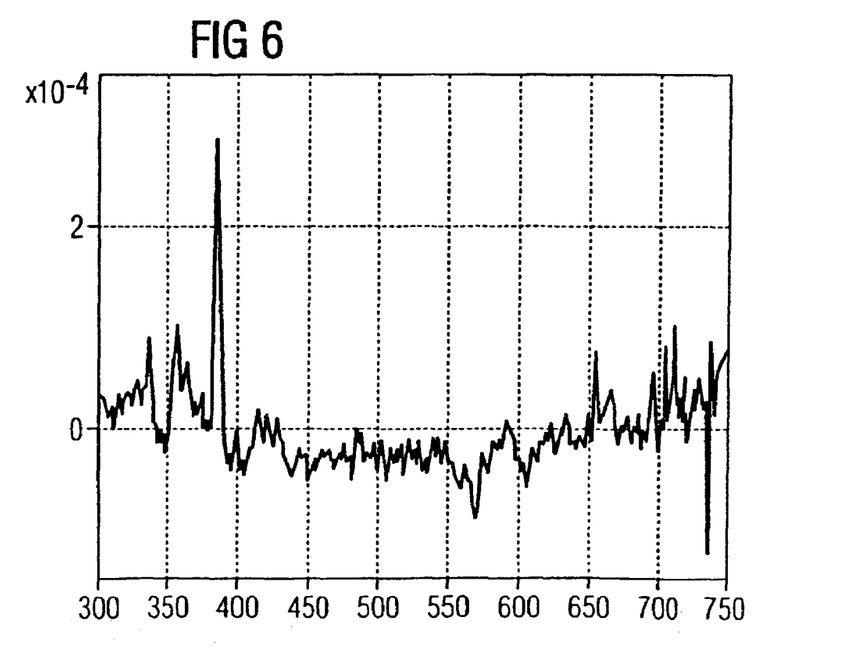
FIG. 6 shows a representation of an end point pattern $u_{EP}$.

FIG. 6 shows a representation of the end point pattern $u_{EP}$. Here, the components $U_{EP}^j$ of the end point pattern $u^{EP}$ are the weights looked for, for the linear combination of the intensities of the measured wavelengths from the emission spectrum. In the present exemplary embodiment, the end point pattern $u_{EP}$ can be assigned a chemical interpretation. In FIG. 6, for example, CN lines and H lines can be seen clearly.

If, then, the end point of an etching operation will be determined during the production of an integrated circuit, then, as described in relation to FIG. 1, the emission spectrum from the plasma etching is measured continuously. From the measured variables, a linear combination y(t) is then formed using the weights $u_{EP}^j$. This can be done, for example, by creating a matrix $\Lambda(\lambda, t)$ from the measured values, and following each measuring time, the end point pattern $u_{EP}$ is multiplied by the transpose of this matrix $\Lambda(\lambda, t)$:

$$y(t)=\Lambda(\lambda,t)^T u_{EP}.$$

Figure 7:
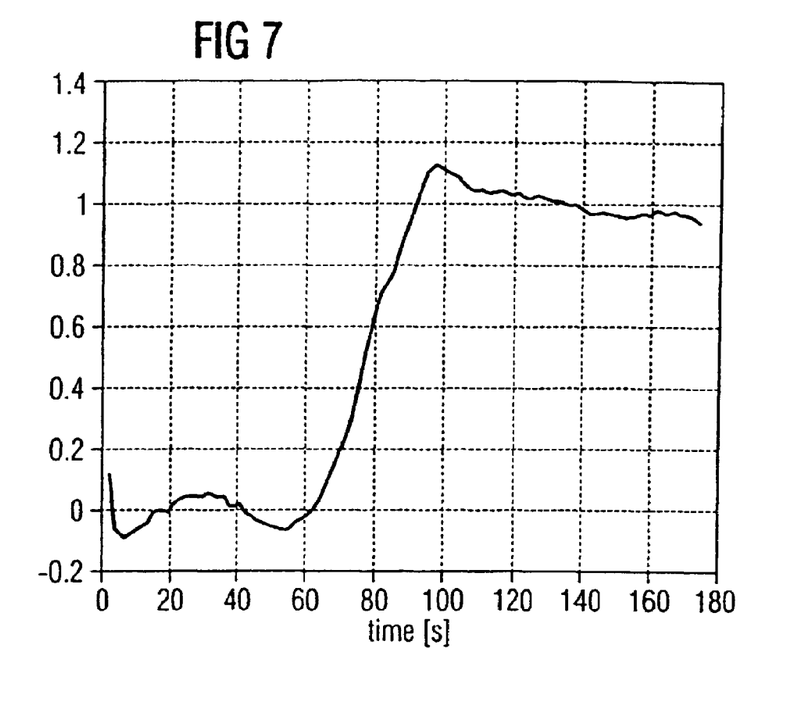
FIG. 7 shows a representation of the linear combination y(t) (generated end point signal) for improving the determination of the end point of a plasma etching operation.
Figure 8:
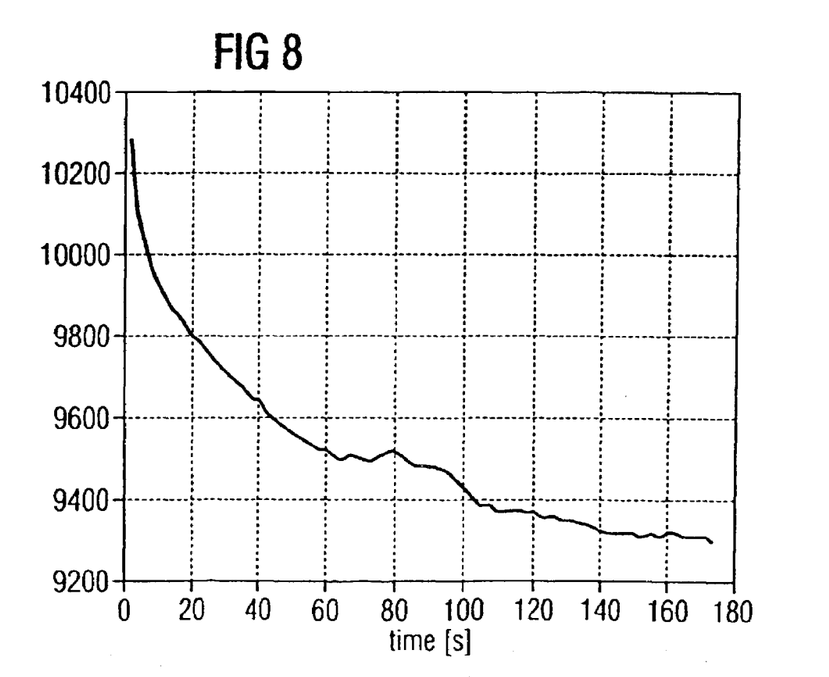
FIG. 8 shows the corresponding conventional signal for determining the end point of a plasma etching operation as known in the prior art.

FIG. 7 shows a representation of the linear combination y(t) for the improved determination of the end point of a plasma etching operation. It can be seen clearly that the linear combination y(t) substantially exhibits a step-like form, which supplies a signal which is substantially sharper and better suited for detecting the correct end point. As a comparison with this, the corresponding conventional end point signal is represented in FIG. 8. In the case of this conventional end point signal, the correct end point must be obtained from the position of the small local maximum in the middle of the signal (at about 80 seconds). The determination of the end point by the conventional method is therefore unreliable.

An evaluation of the linear combination y(t) shown in FIG. 7 then supplies the desired end point of the plasma etching. One possible way of evaluating the linear combination y(t) consists in predefining a threshold value (e.g. 0.6). If the linear combination y(t) exceeds the threshold value, the etching process can either be terminated immediately or after the expiration of a certain, fixedly predefined overetch time.

The predefinition of a threshold value is very simple to implement and supplies satisfactory results for many processes. Unfortunately, this method of determining the characteristic variable generally depends on the absolute magnitudes of the measured value. In the present example, reaching the threshold value depends, for example, on the total intensity of the measured radiation. The total intensity of the measured radiation is a priori unknown, however, so that the correct end point cannot be defined exactly by predefining a threshold value.

Figure 9:
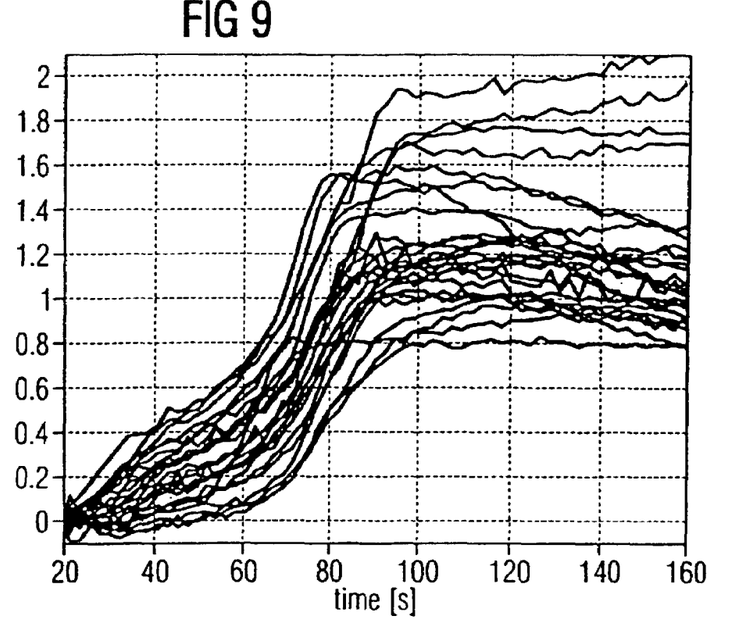
FIG. 9 shows the course of the linear combination y(t) for some product wafers from three different product cycles.
Figure 10:
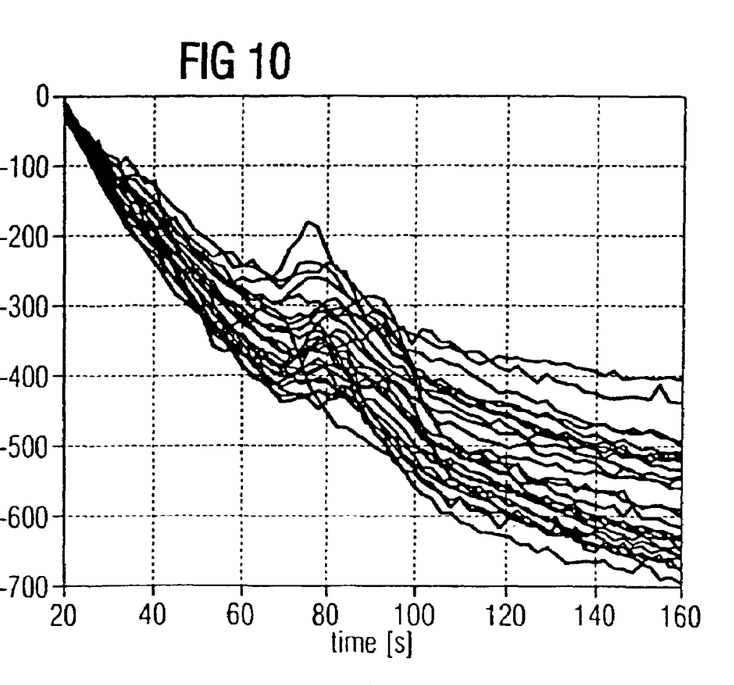
FIG. 10 shows the course of the corresponding conventional signal as known in the prior art.

FIG. 9 shows the course of the linear combination y(t) for some production wafers from three different production cycles. The resultant end point signals show the successful transfer of the end point pattern to other etching operations. In comparison, the conventional end point signals (CN lines) from the corresponding etching operations are represented again in FIG. 10. Although, according to FIG. 9, it has been possible to generate an end point signal that is much sharper as compared with FIG. 10, a quantitative predefinition of a threshold value (of about 0.6) does not lead exactly to the desired end points, since this threshold value is reached sooner or later, depending on the total intensity of the signal. For this reason, a qualitative signal analysis is subsequently carried out.

Figure 11:
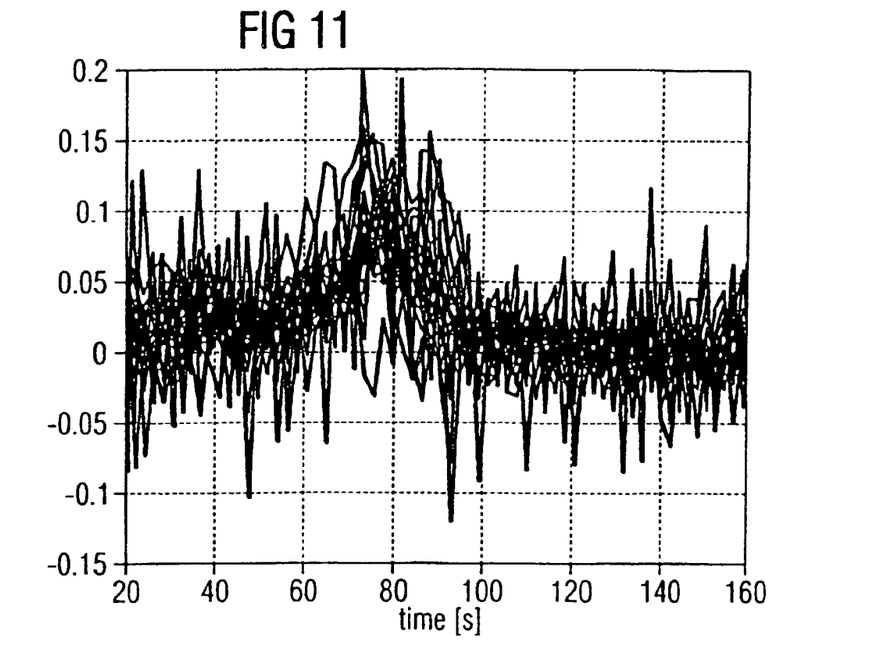
FIG. 11 shows the time derivative of the linear combinations y(t) shown in FIG. 9.

For the accurate definition of the end point, in the following text the point of inflection of the linear combination y(t), that is to say, the maximum of the first derivative of the linear combination y(t) with respect to time is therefore used. As can be seen from FIG. 9, this point of inflection is substantially independent of the total intensity of the measured signal. FIG. 11 shows the time derivative of the linear combinations y(t) shown in FIG. 9. However, it can be seen that because of the noise in the measured variables, the first derivative of the linear combinations y(t) is likewise extremely noisy, so that the maximum of the first derivative cannot be determined in a straightforward way.

Figure 12:
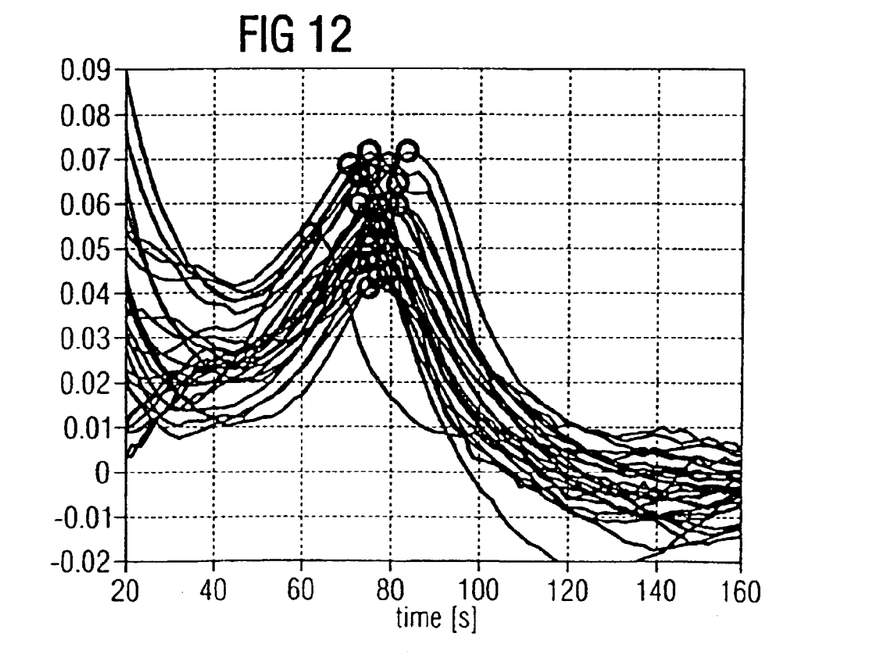
FIG. 12 shows the time derivative of the linear combinations y(t) shown in FIG. 9 following filtering.

For this reason, in the present embodiment, the linear combinations y(t) are first filtered before the first time derivative is formed. By using the filtering, the noise component is suppressed and the actual signal becomes more sharply pronounced. FIG. 12 shows the first derivative of the filtered linear combinations y(t). So that the maximum is not shifted during the filtering, the filtering is carried out with a zero-phase filter, as it is known. In order to filter the linear combination y(t), a series of methods or filters can be used. In the present example, the time-discreet variant (sample time $T_a$) of a Butterworth filter of first order (filter time $T_F$) was used. This filter has the following transfer function C:

$$G = \frac{z\frac{1-a}{2} + \frac{1-a}{2}}{z-a} \text{ with } a = \exp(-T_a/T_F).$$

For the concrete application, a filter time constant $T_F$ of 10s was selected, with a sample time $T_a$ of 2s.

The concrete filtering is carried out by first applying the filter G to the signal y(t) to be filtered. Then, in order to compensate for the phase shift produced during the first filtering, the intermediate signal y* generated in this way is then led via a filter created from the filter G by mirroring the zero and pole positions. Because of the instability of this filter, it is necessary to carry out the implementation in the reverse chronological direction. However, this signifies the same as the renewed application of the original filter G to the signal y* reversed in the chronological direction. The chronological direction of the result of this filtering is then reversed again, in order finally to obtain the desired filtered signal $Y_F$. By using this "double" application of the Butterworth filter of first order, a zero-phase filter is obtained which does not shift the point of inflection of the function y(t). Since operations are generally carried out with a fixed over-etch time, this method can be applied in spite of its chronologically acausal character, which lies in the order of magnitude of the filter time constant.

Figure 13:
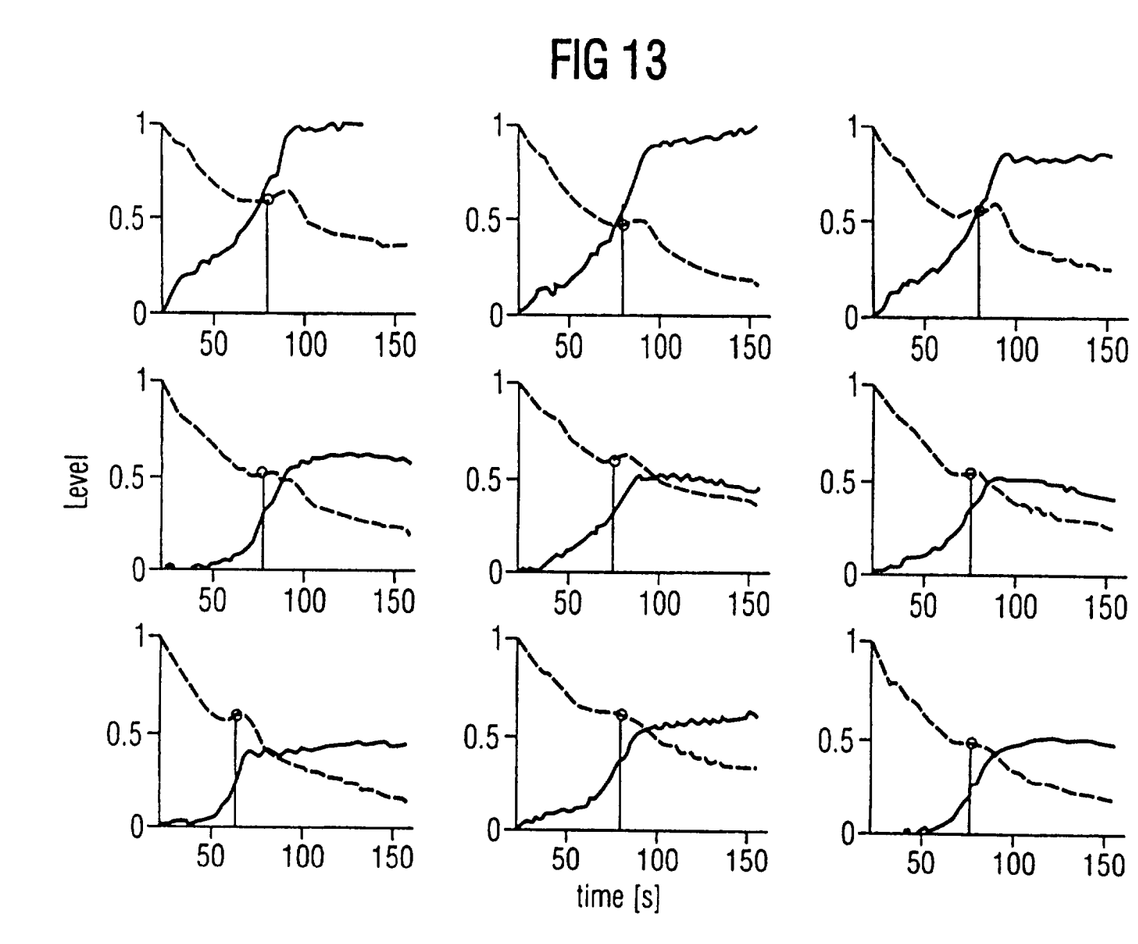
FIG. 13 shows linear combinations y(t) (continuous lines) with the determined end points (circle) for comparison with the conventional CN signals (dashed) according to the prior art.

From the time derivatives of the filtered signals (FIG. 12), the maximum can now be determined (on line), which corresponds to the points of inflection of the linear combinations y(t) from FIG. 9. The fact that the times found are truly end point specific becomes clear from FIG. 13. In addition to the generated end point signal (continuous line) and the determined end point (circle), the conventional CN signal according to the prior art is shown for comparison. It can be seen clearly that the end point detected using the linear combination y(t) always falls on the rise in the CN signal. This rise is to some extent very flat and varies in its shape, so that it cannot be detected in an automated way.

After the expiration of a fixed overetch time, the process can be stopped under end point control with the method presented.

In particular, contact holes with a very small opening ratio can be produced reproducibly and with high quality in this way.

In the embodiment of the method that has been described thus far, only one trial etching operation was used to define the correct weights (coefficients) for the linear combination of the measured variables. In order to increase the robustness of the method, however, it may be expedient to incorporate the results from a number of trial runs or production runs in the definition of the weights (coefficients) for the linear combination. In the present case, for example, the measured spectral matrices from a number of etching operations (e.g. at the start, in the middle and at the end of "wet cleaning cycle" of the reaction chamber) can be included in the definition of the weights.

In order to take a number of trial runs or production runs into account, it is preferable to combine the measured variable matrices from the individual processes into a single, large block matrix. For the example of contact hole etching, this means that a large spectral matrix is formed from n spectral matrices lined up chronologically. This means that for one fixed wavelength (this corresponds to one row of the matrix), the intensity time profiles from the various etching processes are entered one after another into one row of the matrix. If, for example, three trial etching operations are to be taken into account in a manner corresponding with the exemplary embodiment described above, a matrix $\Lambda_O(\lambda, t)$ with 1024 rows and 300 (3*100) columns is produced.

In order to determine the weights of the linear combination y(t), again a singular value decomposition based on the matrix $\Lambda_0(\lambda, t)$, which comprises a number of block matrices $\Lambda_n(\lambda, t)$, can then be carried-out:

$$[\Lambda_1(\lambda, t) | \Lambda_2(\lambda, t) | \ldots | \Lambda_n(\lambda, t)] = U \cdot \Sigma \cdot V^T = \sum_i \sigma_i \cdot u_i(\lambda) \cdot v_i(t)^T$$

Again, the linearly independent spectral basic patterns $u_i$ are contained in the matrix U. However, the vectors $v_i$ now incorporate the time signal components associated with the spectral basic patterns over a number of etching operations. Accordingly, the desired end point signal $Y_{MO}(t)$ must be equipped with n tan h functions arranged one behind another, whose j=1, . . . , n layers $t_{EP}^j$ for each etching operation have to be incorporated in the optimization. As a result of the following optimization of the quality function, n different parameters $t_{EP}^i$ are then obtained, but only one set of optimum coefficients $c^{opt}_i$, from which again an end point pattern $u_{EP}$ can be formed:

$$u_{EP} = \Sigma_i u_i c^{opt}_i.$$

However, the weights $u_{EP}^j$ obtained in this way now contain the information from a number of etching operations, so that the method can, for example, be used stably over a relatively long time period.

We claim:

1. A method of monitoring a production process, which comprises:
    determining intensities of various wavelengths in an emission spectrum at predefined times;
    forming at least one linear combination from the intensities of various wavelengths, and selecting weights of the linear combination such that a predefined curve shape is approximated; and
    determining at least one characteristic variable from the linear combination.

2. The method according to claim 1, wherein: the intensities of the various wavelengths are in a spectral range between 200 nm and 950 nm.

3. The method according to claim 1, wherein: the emission spectrum is an emission spectrum of a plasma process.

4. The method according to claim 3, wherein: the characteristic variable is an end point of the plasma process.

5. The method according to claim 1, which comprises: using a step-like function as a predefined curve shape.

6. The method according to claim 5, wherein: the step-like function has at least one free parameter to match to the characteristic variable that will be determined.

7. The method according to claim 1, which comprises:
    determining the weights of the linear combination by configuring the intensities of various wavelengths in a matrix and performing a principal component analysis based on the matrix.

8. The method according to claim 7, which comprises:
    using a singular value decomposition to perform the principal component analysis.

9. The method according to claim 1, which comprises:
    determining the weights of the linear combination by minimizing a function based on the predefined curve shape and the linear combination.

10. The method according to claim 9, which comprises: as a result of the minimizing of the function, determining important principal components of a measured variable matrix to approximate the predefined curve shape.

11. The method according to claim 9, which comprises: as a result of the minimizing of the function, determining a free parameter of a step-like function.

12. The method according to claim 1, which comprises: determining the weights of the linear combination by maximizing a function based on the predefined curve shape and the linear combination.

13. The method according to claim 1, which comprises: performing the determining of the characteristic variable by smoothing the linear combination.

14. The method according to claim 13, which comprises: using a zero-phase filter to perform the smoothing of the linear combination.

15. The method according to claim 1, which comprises: performing the determining of the characteristic variable by using qualitative criteria.

16. The method according to claim 1, which comprises:
    obtaining the intensities of various wavelengths from a plurality of runs selected from a group consisting of trial runs and production runs; and
    determining the weights of the linear combination by using the intensities of various wavelengths.

17. The method as claimed in claim 16, which comprises:
    determining the weights of the linear combination by configuring intensities of various wavelengths from a plurality of runs, selected from a group consisting of trial runs and production runs, in a matrix and performing a principal component analysis based on the matrix.

18. The method according to claim 1, wherein: the emission spectrum of a plasma etching process is used.

19. The method according to claim 1, wherein: the various wavelengths include a large number of wavelengths.

20. A method of monitoring a production process, which comprises:
    determining intensities of various wavelengths in an emission spectrum of a plasma process at predefined times;
    forming at least one linear combination from the intensities of various wavelengths, and selecting weights of the linear combination such that a predefined curve shape is approximated; and
    determining an end point of the plasma process from the linear combination.

* * * * *

UNITED STATES PATENT AND TRADEMARK OFFICE
CERTIFICATE OF CORRECTION

| | | |
|---|---|---|
| PATENT NO. | : 7,479,395 B2 | Page 1 of 1 |
| APPLICATION NO. | : 10/205080 | |
| DATED | : January 20, 2009 | |
| INVENTOR(S) | : Ferdinand Bell et al. | |

It is certified that error appears in the above-identified patent and that said Letters Patent is hereby corrected as shown below:

Column 9,

Line 67, "This filter has the following transfer function C:" should read

-- This filter has the following transfer function G: --

Signed and Sealed this

Fourteenth Day of September, 2010

David J. Kappos
*Director of the United States Patent and Trademark Office*